United States Patent [19]
Zanger

[11] Patent Number: 5,342,293
[45] Date of Patent: Aug. 30, 1994

[54] VARIABLE VACUUM/VARIABLE FLOW PHACOEMULSIFICATION METHOD

[75] Inventor: Frank Zanger, Hayward, Calif.

[73] Assignee: Allergan, Inc., Irvine, Calif.

[21] Appl. No.: 81,435

[22] Filed: Jun. 22, 1993

[51] Int. Cl.⁵ .............................................. A61B 17/20
[52] U.S. Cl. ...................................... 604/22; 604/28; 604/30
[58] Field of Search ................ 604/22, 27, 28, 30–34, 604/49, 118–120; 128/24 AA, 898

[56] References Cited

U.S. PATENT DOCUMENTS

| | | | |
|---|---|---|---|
| 3,589,363 | 6/1971 | Banko et al. | 604/22 |
| 3,693,613 | 9/1972 | Kelman | 604/22 |
| 4,184,510 | 1/1980 | Murry et al. | 604/22 |
| 4,274,411 | 6/1981 | Dotson, Jr. | 604/30 |
| 4,369,785 | 1/1983 | Rehkopf et al. | 604/35 |
| 4,764,165 | 8/1988 | Reimels et al. | 604/22 |
| 4,798,580 | 1/1989 | DeMeo et al. | 604/30 |
| 4,832,685 | 5/1989 | Haines | 604/30 |
| 4,983,901 | 1/1991 | Lehmer | 318/685 |
| 5,084,012 | 1/1992 | Kelman | 604/28 |
| 5,154,696 | 10/1992 | Shearing | 604/22 |

*Primary Examiner*—C. Fred Rosenbaum
*Assistant Examiner*—Michael Rafa
*Attorney, Agent, or Firm*—Walter A. Hackler

[57] ABSTRACT

A method useful in a process for cataractous lens removal for operating phacoemulsifier apparatus having a vacuum pump and a fluid irrigation pump in order to simultaneously control vacuum, for aspiration, and fluid flow, for irrigation, to a phacoemulsifier handpiece. The method includes selecting a vacuum limit for aspiration; selecting a fluid flow limit for irrigation; assigning a linear relationship between a remotely disposed control lever and vacuum provided to the handpiece by the vacuum pump between zero and the vacuum limit; supplying vacuum to the handpiece by actuating the control lever; and controlling the fluid flow to the handpiece in response to the level of vacuum provided to the handpiece so that as more vacuum is provided, less fluid flow than the fluid flow limit is provided to the handpiece.

8 Claims, 2 Drawing Sheets

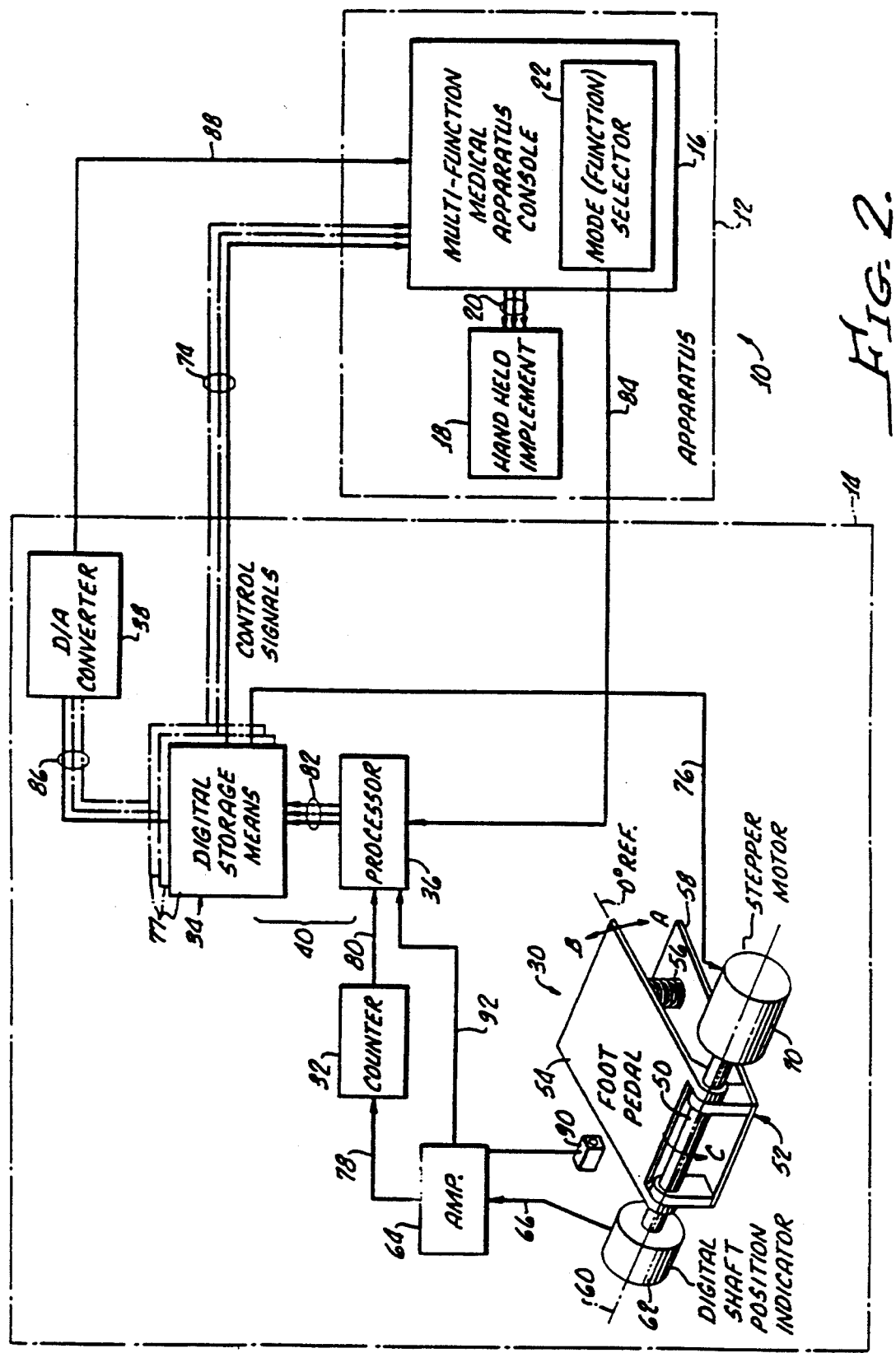

VARIABLE VACUUM/VARIABLE FLOW PHACOEMULSIFICATION METHOD

The present invention generally relates to ophthalmic surgery and is more particularly directed to a method for insertion, phacoemulsification, irrigation, and aspiration of a cataractous lens.

Cataracts are the leading cause of blindness in humans. The cataractous lens is one that has become opaque or cloudy which inhibits its function of transmitting and focusing light in the eye. This condition may be corrected by surgically removing the cataractous lens and replacing it with an artificial intraocular lens.

A number of medically recognized techniques have been utilized for lens removal and among these, a popular technique is phacoemulsification, irrigation and aspiration. This method includes the making of a corneal incision, which is typically cauterized to reduce bleeding, and the insertion of a handheld surgical implement which includes a needle which is ultrasonically driven in order to emulsify the eye lens. Simultaneously with this emulsification, a fluid is inserted for irrigation of the emulsified lens and a vacuum provided for aspiration of the emulsified lens and inserted fluids.

Many surgical instruments and controls in use today linearly control the vacuum or linearly control the flow of irrigation fluid. This feature allows the surgeon to precisely "dispense" or control the "speed" at which he/she employs, either the vacuum or the flow, but not both. However, there often are times during surgery when the precise control when one of the two variables (vacuum or fluid) is desired over the other. The experienced user, understanding the relationship between the vacuum and the flow, may manually adjust the preset variable appropriately at the console in order to obtain an acceptable performance. However, if this adjustment is overlooked, then the combination of both high vacuum and high flow can cause undesirable fluidic surges at the surgical site with possible damage inflicted on the patient.

It should be apparent that the control of handheld surgical instruments for use in phaco surgery is complex. Phacoemulsifier apparatus typically comprises a cabinet, including a power supply, vacuum pump, electronic and associated hardware and a connected, multifunction and handheld surgical implement, including a hollow slender-like needle tube as hereinabove described, in order to perform the phacoemulsification of the cataractous lens.

It should be appreciated that a surgeon utilizing the handheld implement to perform the functions hereinabove described requires easy and accessible control of these functions, as well as the ability to selectively shift or switch between at least some of the functions (for example, irrigation and irrigation plus aspiration) as may arise during phacoemulsification surgery.

In view of the difficulty with adjusting cabinet-mounted controls, while operating an associated handheld medical implement, foot pedal control systems have been developed such as described in U.S. Pat. No. 4,983,901. This patent is to be incorporated entirely into the present application, including all specification and drawings for the purpose of providing a background to the complex controls required in phacoemulsification surgery and for describing apparatus which may be utilized or modified for use with the method of the present invention.

To further illustrate the complexity of the control system, reference is also made to U.S. patent application Ser. No. 961,138, filed Oct. 14, 1992, for "Foot Pedal Control with User Selectable Operational Ranges". This patent application is to be incorporated in the present application by this specific reference thereto, including all specifications and drawings for the purpose of further describing the state of the art in the field of this invention.

Further procedures and problems in connection with phacoemulsification, irrigation and aspiration methods and apparatus are discussed in U.S. Pat. No. 5,154,696.

Regarding the control of vacuum and irrigation fluid flow through the use of foot pedals, prior art devices have controlled the vacuum through incremental depressions of the foot pedal in a linear fashion, but the fluid flow, or pump speed, is either on or off. Depending upon the rate or preset speed of the pump, this may cause undesirable effects on or trauma to ocular structures or tissues, such as, for example, corneal collapse and endothelium damage or severe and rapid chamber shallowing.

The present invention provides a method in which the surgeon may precisely control either the vacuum or the fluid flow with a non-chosen variable being automatically balanced.

SUMMARY OF THE INVENTION

A method in accordance with the present invention defines suitability and a process for cataractous lens removal and more particularly pertains to the operation of phacoemulsifier apparatus having a vacuum pump and a fluid irrigation pump, in order to simultaneously control vacuum, aspiration, and fluid flow for irrigation to a phacoemulsifier handpiece. The method generally comprises selecting a vacuum limit for aspiration, selecting a fluid flow limit for irrigation, and thereafter assigning a linear relationship between a remotely disposed control lever and vacuum provided to the handpiece by the vacuum pump between zero and vacuum limit.

Thereafter, the fluid flow to the handpiece is controlled in response to the level of vacuum provided to the handpiece so that as more vacuum is provided, less fluid flow than the fluid flow limit is provided to the handpiece.

More particularly, the fluid flow may be controlled linearly in response to the level of vacuum.

Alternatively, in accordance with the present invention, the method may include assigning a linear relationship between a remotely disposed lever and fluid flow provided to the handpiece by an irrigation pump between zero and the fluid flow limit and controlling the vacuum to the handpiece in response to the amount of fluid flow provided to the handpiece so that as more fluid flow is provided, less vacuum than the vacuum limit is provided to the handpiece.

BRIEF DESCRIPTION OF THE DRAWINGS

The advantages and features of the present invention will be better understood by the following description when considered in conjunction with the accompanying drawings in which:

FIG. 2 is a block diagram of the control system in accordance with the present invention.

DETAILED DESCRIPTION

Figure 1:
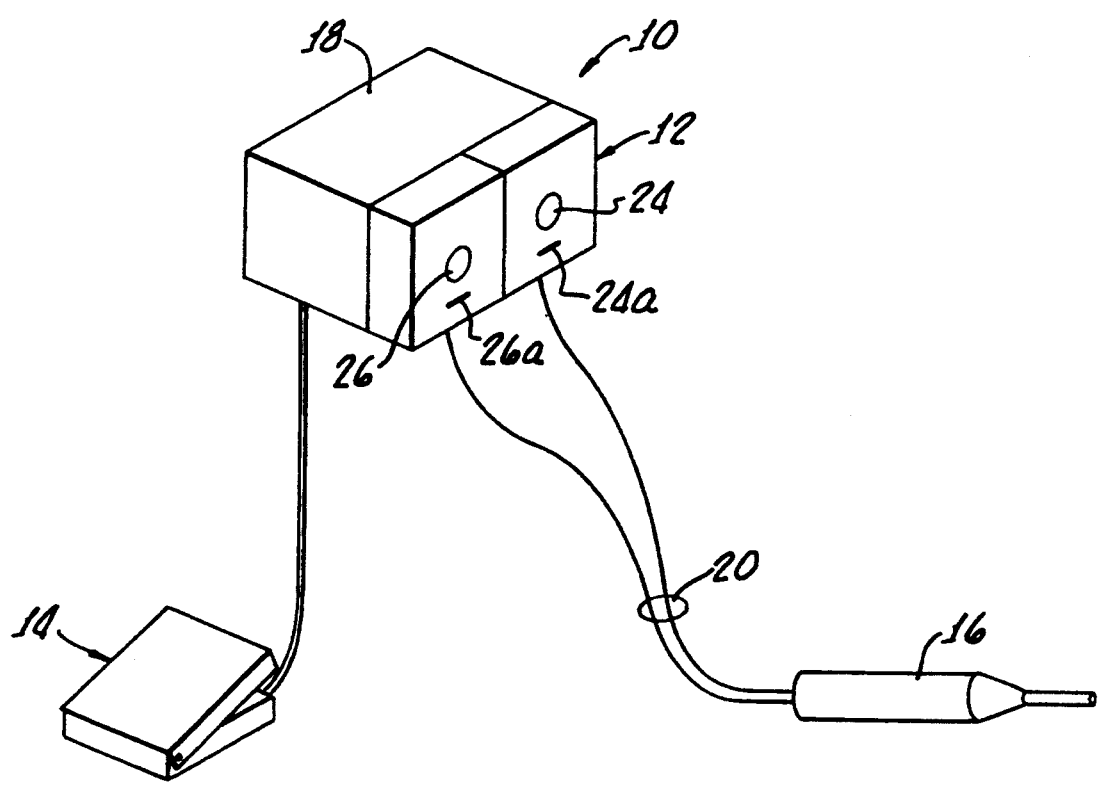
FIG. 1 is a diagrammatic view of apparatus suitable for the performance of the present invention which generally includes a control system, a remotely disposed foot pedal, and a phacoemulsifier handpiece.

FIG. 1 shows a prior art medical equipment system 10 suitable for use in the present invention. The system 10 generally comprises a medical apparatus 12 having operatively connected thereto a digital electronic foot control 14 and a phacoemulsifier handpiece 16 of conventional design. Medical apparatus 12 is a multi-function medical phacoemulsifier. The apparatus 12 includes an equipment console or cabinet 18 constructed for housing all of the equipment necessary for enabling the functioning of medical apparatus 12 in a prescribed manner through handheld implement 16. The console 18 may, for example, include a power supply, a vacuum pump, a source of ultrasonic power, a fluid irrigation pump, a source of irrigating fluid, and various other hardware and electronic circuits, none of which are shown as they do not form any part of the present invention. A full explanation of this system is found in U.S. Pat. No. 4,983,401 which is incorporated herein, including all drawings and specification for the purpose of describing the type of equipment suitable for the method of the present invention. The handpiece 16 is operably connected to the console by an umbilical 20 typically several feet in length. The umbilical 20 includes both vacuum and irrigation line as well as an electrical cable.

A suitable foot pedal control system 14, for use in the method of the present invention is depicted in FIG. 2. More particularly described below are foot pedal means or assembly 30, a digital counter 32, digital storage means 34, data processor means 36, and digital-to-analog (D/A) converter 38. Together, digital storage means 34 and data processor means 36 can be considered to form a logic means 40.

As further illustrated in FIG. 2, the medical apparatus 12 may be a multi-function apparatus, and console 18 may include a manually-operated function or mode selector 22 through which the various operational functions or modes of operation are selected. That is, manual controls 24, 24a, 28, 28a are used to preset or select a vacuum limit and/or a flow rate limit and assign a relationship, preferably a linear relationship, between the vacuum and flow rate.

Foot pedal assembly 30 comprises a pedal shaft 50 which is rotationally mounted in a pedal housing or mount 52, only part of which is shown in FIG. 2. Non-rotatably fixed to central regions of pedal shaft 50 is a foot pedal 54 which is biased or urged, for example, by a spring or springs 56, to a zero-rotational reference position (that is, the undepressed position).

In operation, foot pedal 54 is depressed by an operator's foot downwardly (direction of Arrow A) toward a housing base plate 58, spring 56, when foot pressure on pedal 54 is released, returning the pedal (in the direction of Arrow B) to the zero reference position.

Non-rotatably connected to one end region of pedal shaft 50, on a shaft rotational axis 60, is a bidirectional digital rotational position detector or shaft encoder 62, which may be of a known type. Shaft encoder 62 may be connected to pedal shaft 50 through a drive, for example, a 5:1 speed-up drive (as described below).

As pedal 54 is depressed from the zero reference position, digital position detector 62 provides a digital signal to an amplifier 64, over a conduit 66, the digital signal containing data relative to the rotational motion of pedal shaft 50 relative to the zero reference position. Detector 62 may, for example, be configured for providing a series of N outputs corresponding to N-given angular positions of foot pedal.

Connected to the opposite end region of pedal shaft 50, also along shaft axis 60, are motor means 70, which preferably comprise a stepper motor of a known type. Motor means 70 are importantly connected for driving pedal shaft 50 in a counterclockwise or "return" direction (see Arrow C) when the motor means are energized (as described below) at one or more preselected (given) pedal angular positions relative to the zero reference position, according to the particular function or functions to be performed by implement 18.

At pedal rotational positions at which motor means 70 are energized, an operator is required to apply additional foot pressure on pedal 54 to overcome the driving torque on shaft 50 provided by motor means, the increased foot pressure required to depress foot pedal 54 serving to alert the operator that some preestablished or given event, such as the switching from one operational function to another, will occur if the foot pedal is depressed further.

As is described below, motor means 70 can be programmed to be energized at any desired angular position of foot pedal 54, and the angular foot pedal positions at which motor means 70 is energized may be different for different functions to be controlled by foot pedal control system 14.

As hereinabove noted, an ophthalmic surgeon performing phacoemulsification surgery ordinarily employs the following sequence of operations or functions:
  I) irrigation of the eye with a saline solution;
  II) a combination of simultaneous irrigation and aspiration of the irrigating fluid;
  III) a combination of fluid irrigation of the patient's eye, the ultrasonic emulsification of the eye lens, and the aspiration of the irrigation fluid and broken up particles of the lens; and
  IV) cautery.

During this process, the surgeon may, however, want the option of switching back to just fluid irrigation and fluid aspiration without lens emulsification. These functions are referred to as modes and are selected at the front panel of console 18 and are directed to foot pedal processor 40 by mode selector 22.

The foot pedal control system 14 provides the functional operation of handpiece 16 for each of the hereinabove identified modes. Accordingly, the logic means 40 provides the necessary functional control signals to console 18 (over a conduit or group of conduits 74) so that, for example, at a certain predetermined (and convenient) angular position of foot pedal 54, a signal is provided by logic means 40 "directing" console 18 to provide a flow of irrigating fluid to handpiece 16 and, at another predetermined angular position of the foot pedal, to provide emulsifying ultrasonic energy to the implement.

It is, of course, to be understood that the control provided by foot pedal control system 14 to handpiece 16, through console 18, should be repeatable. That is, certain specific control signals should be provided by foot pedal control system 14 whenever foot pedal 54 is at a specific angular position, and the same sequence of signals should be provided at the same position whenever the foot pedal is depressed.

The function of foot pedal shaft position indicator or encoder 62 and counter 32 is to precisely, accurately, and repeatably provide to logic means 40 digital output signals which correspond to and are representative of the angular position of foot pedal 54 relative to its zero (undepressed) position. Encoder 62 provides signals which are decoded by counter 32 into increment or decrement events. In this manner, counter 32 provides a numerical representation of the angular position of foot pedal 54, such representation being used by processor 36 as a pointer into digital storage means 34.

Based upon "learning" from pedal shaft position indicator 62 the exact angular position of foot pedal 54, it is a function of logic means 40 to provide to console 18 the requisite control signals associated with that foot pedal position. Another function of logic means 40 is to provide energizing signals to motor means 70, over a conduit 76, whenever pedal shaft indicator means 62 signals the logic means that pedal 54 is at a predetermined angular position at which the energizing of motor means is required to provide pedal back pressure.

Accordingly, memory means 34 is configured for storing whatever predetermined sets of control signs are needed to be provided to console 18 as foot pedal 54 is depressed from its zero (at rest) position to its fully depressed position.

Preferably, the memory means 34 is configured for storing N sets of given control signals to be provided to console 18 for N corresponding angular positions of foot pedal 54 (that is, of pedal shaft 50) as detected or determined by position indicator 62 and counter 32. Generally, among some of the N sets of given control signals stored in storage means 34 are one or more control signals causing the energizing of motor means 70 at given pedal shaft angular positions.

Memory means 34 may advantageously be in the form of an address card 77 having N addresses, and in which, each address corresponds to a particular one of the N angular positions of foot pedal 54 (that is, of pedal shaft 50). In each of the N address positions of address card 77, there is stored the set of digital output control signals required for the corresponding pedal shaft position. Processor 36 functions to decode the signals from shaft angular position indicator 62 and, in conjunction with counter 34, provides a corresponding address "pointer" into address card 77.

Thus, when foot pedal 54 is depressed by an operator, position indicator 62 provides a series of output signals which are counted by counter 32 to produce data related to the angles through which pedal shaft 50 is rotated. These output signals are provided over a conduit 78 to counter 32 which, responsive thereto, provides digital counts over a conduit 80 to processor 36.

Responsive thereto, processor 36 provides a corresponding sequence of address "pointers" over a conduit 82 to memory means 34 (that is, to address card 77), each of these address pointers corresponding to a particular angular position of pedal shaft 50, as determined by position indicator 62. Whenever an address pointer is received by storage means 34, the set of control signals in the address "pointed" to is outputted over conduit 74 to console 18, wherein the control signals are used to control functions of apparatus 12 in a given manner.

In addition to providing particular output control signals to console 18, storage means 34 preferably provides particular digital output signals (according to the accessed addresses in the storage means) over a conduit 86 to digital-to-analog (D/A) converter 38. A corresponding analog signal is provided from D/A converter 38 over a conduit 88 to console 18 for the operation of variable controls in apparatus 12, such as emulsification power which is responsive to an analog voltage signal.

A reset switch 90, preferably of the optical type, is mounted adjacent to foot pedal 54 and is connected to processor 36 and counter 32 (through amplifier 64) by a conduit 92 for resetting the processor when the foot pedal is at its zero position. This resets counter 32 when pedal 54 is at the zero position.

The use of a plurality of similar address cards 77 to comprise storage means 34 is advantageous, since each address card can be provided with N sets of given sets of output control signals (corresponding to N different addresses and N given foot pedal angular positions) appropriate for a particular function (or group of functions) which apparatus 12 is required to perform through handheld implement 18. The appropriate address card 77 is selected, through processor 36, by function selector 22 on console 18 when a given function (or group of functions) of the apparatus is selected.

For example, in the case of a phacoemulsifier, one function is irrigation only, another is irrigation and aspiration and emulsification, another is phacoemulsification, and still another is cautery. Once a particular function (or group of functions) is selected by selector 22, the corresponding address card 77 in storage means 34 is concurrently selected so that as address pointers are generated in processor 36 (as above-described), the address pointers are directed to the selected address card whose N sets of output control signs are appropriate for the selected function.

As a consequence, the selection of a particular address card 77 in storage means 34 in effect reprograms the control provided by foot pedal 54. That is, the full travel of foot pedal provides N particular sets of given out control signals to console 18 when one address card 77 is selected; and another, different set of control signals to the console when another address card is selected; still another N set of output control signals when still another address card is selected; and so on.

By way of illustrative example, this reprogramming of foot pedal 54 is depicted for a phacoemulsifier in the following Table, which shows the different operations enabled by the foot pedal as a function of foot pedal travel. Although, as shown in the Table, functions within operations switch at the same pedal positions for all the operations, it is to be understood that, if desired, address cards 77 can be programmed so that there is no such uniformity.

|  | FOOT SWITCH POSITION | | | |
| --- | --- | --- | --- | --- |
| Function | a | b | c | d |
| Irrigation/ Aspiration | No Function | Irrigation | Irrigation/ Aspiration | Irrigation/ Aspiration |
| Phacoemulsion | No Function | Irrigation | Irrigation Aspiration | Irrigation/ Aspiration/ Emulsification |
| Phacoemulsification | No Function | Irrigation | Irrigation/ Aspiration/ Cutting | Irrigation/ Aspiration/ Cutting |
| Wet Field Cautery (Voltage) | No Function | Cautery | Cautery | Cautery |

When both irrigation and aspiration (vacuum) are selected, the method of the present invention utilizes the controls 24 to select a vacuum limit for aspiration and control 26 to select a fluid flow limit for irrigation. Thereafter, control 24a may be used to assign a linear relationship between the foot pedal 54 and the vacuum provided to the handpiece 16. As the foot pedal 54 is depressed, vacuum is supplied to the handpiece and through the processor 36 and storage means 34. The programmed storage means 34 thus controls the fluid flow to the handpiece 16 in response to the level of vacuum provided to the handpiece 16 so that as more vacuum is provided, less fluid flow is provided to the handpiece. Alternatively, the vacuum supplied to the handpiece 16 may be controlled by the storage means 34 in response to fluid flow to the handpiece 16.

For purposes of better illustrating the present invention relating to foot pedal control system 14, counter 32, digital storage means 34, processor 36, and D/A converter 38 are shown and described above as being separate from one another and from apparatus 12, as may sometimes be advantageous.

However, it is to be appreciated that such is not necessarily the case and that counter 32, storage means 34, processor 36, and/or D/A converter may alternatively be integrated together and/or may alternatively be fully integrated into apparatus 12, for example, into console 18.

It is also to be appreciated that amplifier 64, although shown in FIG. 2 as being separate from foot pedal assembly 30, may advantageously be integrated thereinto so as to form a convenient, compact unit. The purpose of amplifier 64 is to enable conduits 78 and 92 to be of substantial length with the majority of components being remote from foot pedal assembly 30.

Moreover, although conduits 76, 78 and 92 are depicted in FIG. 2 as being separate conduits, it will be appreciated that, in practice, such conduits would be bundled together in a single cable assembly connected to foot pedal assembly 30.

Conventional use of the hereinabove referenced apparatus provides for three foot pedal operational ranges hereinabove identified. Traditionally, these three ranges were established with equal amounts of travel or foot pedal arc. Specifically, the total amount of foot pedal arc of 15° was equally divided by equal amounts of 5° of travel for each of the three modes. In the case of cautery, the voltage provided to the handpiece is controlled by depressing the foot pedal 54. The cauterization by a conventional handpiece itself is a well-known technique.

Although there has been hereinabove described a variable vacuum/variable flow phacoemulsification method in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. In a process for cataractous lens removal, a method for operating phacoemulsifier apparatus having a vacuum pump and a fluid irrigation pump in order to simultaneously control vacuum, for aspiration, and fluid flow, for irrigation, to a phacoemulsifier handpiece, said method comprising:
   selecting a vacuum limit for aspiration;
   selecting a fluid flow limit for irrigation;
   assigning a linear relationship between a remotely disposed control lever and vacuum provided to the handpiece by the vacuum pump between zero and the vacuum limit;
   supplying vacuum to the handpiece by actuating the control lever; and
   controlling the fluid flow to the handpiece linearly in response to the level of vacuum provided to the handpiece so that as more vacuum is provided, less fluid flow than the fluid flow limit is provided to the handpiece.

2. The method according to claim 1 wherein the control lever is a foot pedal and the method comprises depressing the foot pedal to supply vacuum to the handpiece.

3. The method according to claim 2 wherein the supply of vacuum and fluid flow are provided through separate tubes.

4. The method according to claim 3 further comprising the step of applying voltage to the handpiece for cautery.

5. In a process for cataractous lens removal, a method for operating phacoemulsifier apparatus having a vacuum pump and a fluid irrigation pump in order to simultaneously control vacuum, for aspiration, and fluid flow, for irrigation, to a phacoemulsifier handpiece, said method comprising:
   selecting a vacuum limit for aspiration;
   selecting a fluid flow limit for irrigation;
   assigning a linear relationship between a remotely disposed control lever and fluid flow provided to the handpiece by the irrigation pump between zero and the fluid flow limit;
   supplying fluid flow to the handpiece by actuating the control lever; and
   controlling the vacuum to the handpiece linearly in response to the amount of fluid flow provided to the handpiece so that as more fluid flow is provided, less vacuum than the vacuum limit is provided to the handpiece.

6. The method according to claim 5 wherein the control lever is a foot pedal and the method comprises depressing the foot pedal to supply fluid flow to the handpiece.

7. The method according to claim 6 wherein the supply of vacuum and fluid flow are provided through separate tubes.

8. The method according to claim 7 further comprising the step of applying voltage to the handpiece for cautery.

* * * * *